(12) United States Patent
Nakatani

(10) Patent No.: US 7,748,894 B2
(45) Date of Patent: Jul. 6, 2010

(54) THERMAL ANALYSIS EQUIPMENT

(75) Inventor: Rintaro Nakatani, Chiba (JP)

(73) Assignee: SII NanoTechnology Inc. (JP)

( * ) Notice: Subject to any disclaimer, the term of this patent is extended or adjusted under 35 U.S.C. 154(b) by 366 days.

(21) Appl. No.: 11/661,638

(22) PCT Filed: Aug. 26, 2005

(86) PCT No.: PCT/JP2005/015505

§ 371 (c)(1),
(2), (4) Date: Apr. 26, 2007

(87) PCT Pub. No.: WO2006/025268

PCT Pub. Date: Mar. 9, 2006

(65) Prior Publication Data

US 2008/0025367 A1    Jan. 31, 2008

(30) Foreign Application Priority Data

Sep. 3, 2004    (JP)    .............................. 2004-257133

(51) Int. Cl.
 *G01J 5/00* (2006.01)
 *G01N 25/20* (2006.01)
 *G01J 1/00* (2006.01)
(52) U.S. Cl. .................. 374/11; 374/121; 374/141; 374/5; 250/339.06; 250/336.1; 219/200
(58) Field of Classification Search ............. 250/338.1, 250/339.01, 339.02, 339.04, 339.06, 339.11, 250/340, 340.1, 341.1, 341.6, 341.8, 336.01; 219/698, 710, 711, 712, 200, 201
See application file for complete search history.

(56) References Cited

U.S. PATENT DOCUMENTS

| | | | | |
|---|---|---|---|---|
| 5,133,605 A | * | 7/1992 | Nakamura | 374/124 |
| 5,983,711 A | * | 11/1999 | Pappas et al. | 73/76 |
| 6,860,192 B2 | * | 3/2005 | Sharpe | 99/342 |
| 7,025,499 B2 | * | 4/2006 | Brinz | 374/56 |
| 7,137,734 B2 | * | 11/2006 | Muehlig et al. | 374/27 |
| 2005/0265423 A1 | * | 12/2005 | Mahowald et al. | 374/121 |

FOREIGN PATENT DOCUMENTS

JP    08327573    12/1996

* cited by examiner

*Primary Examiner*—Gail Verbitsky
(74) *Attorney, Agent, or Firm*—Adams & Wilks (57) ABSTRACT

A thermal analysis equipment includes a thermal analysis data preservation function that preserves, as thermal analysis data, signals from a temperature sensor and a physical quantity sensor that detect a temperature and a change in physical quantity, respectively, of a sample. An electromagnetic-wave data acquisition control function controls acquisition of electromagnetic wave data in accordance with setting of a trigger to acquire the electromagnetic wave data. An electromagnetic-wave data preservation function preserves the electromagnetic wave data. An electromagnetic-wave data correlation function correlates the preserved electromagnetic wave data to a position on the thermal analysis data when the trigger is set.

19 Claims, 6 Drawing Sheets

THERMAL ANALYSIS EQUIPMENT

CROSS-REFERENCE TO RELATED APPLICATIONS

This application is a U.S. national stage application of International Application No. PCT/JP2005/015505, filed Aug. 26, 2005, claiming a priority date of Sep. 3, 2004, and published in a non-English language.

TECHNICAL FIELD

The present invention relates to a thermal analysis equipment, which acquires data of electromagnetic waves, such as a sample picture, a sample spectrum, etc. during thermal analysis, from a sample in a less storage capacity without an unexpected defeat through carelessness and can readily relate results of detection of electromagnetic waves and results of thermal analysis to each other.

BACKGROUND ART

Thermal analysis is a technique that measures a certain physical property of a sample as a function of temperature while varying the sample in temperature according to a predetermined program. As temperature changes, a sample undergoes a phase change such as melting, vaporization, etc. and a shape change such as expansion, contraction, etc. A change of state of a sample is widely and further deeply analyzed by preserving data of electromagnetic waves, such as a sample picture, etc. before and after the phase change or the shape change, from a sample to analyze the same together with data of thermal analysis.

In a conventional thermal analysis equipment, sample pictures are stored in a medium such as video tape recorder, etc. for continuous recording, and no specific consideration is taken in relating storage capacity and results of thermal analysis with each other (for example, see JP-A-8-327573 (page 2 to 3, FIG. 1)).

SUMMARY OF THE INVENTION

In thermal analysis, measurements over a long term of one hour or longer are generally made but phase change and shape change, which constitute the key to analysis of a change of state of a sample, occur discretely only several times. Accordingly, it is unnecessary to preserve data of electromagnetic waves continuously over whole limits of measuring time for thermal analysis.

In a conventional thermal analysis equipment, since sample pictures, etc. are stored in a video tape recorder, etc., they are recorded over whole limits of measuring time. When such pictures are digitized in order to combine with data of thermal analysis for ease handling, a very large storage capacity is needed so as to increase requirements for resources and a processing capability of a computer, which handles sample pictures, etc. and data of thermal analysis.

When sample pictures, etc. and data of thermal analysis are combined together to make a report or the like, there is also caused a problem that it is necessary to combine a plurality of commercial softwares to use the same and a work takes a considerable time together with sample pictures of a large capacity. On the other hand, in order to restrict sample pictures in storage capacity, there is a method of indicating necessary locations to store the same while visually observing a sample picture during measurements, but it is necessary to visually observe a sample picture for a long time, so that there is caused a problem of a very large load on a user.

It is an object of the invention to solve the foregoing problems and to provide a thermal analysis equipment in which even when measurements are made over a term of one hour or longer, a load on a user in acquisition of a picture is small and sample pictures, etc. are acquired in a less storage capacity without an unexpected defeat through carelessness. Further, it is an object of the invention to provide a thermal analysis equipment in which even when sample pictures and data of thermal analysis are combined after measurements to make a report or the like, a sample picture related to that point on data of thermal analysis, to which attention is paid, is quickly extracted from many sample pictures to enable readily realizing a report.

Furthermore, the above object is not limited to a sample picture, but also applies to the case where thermal analysis such as acquisition of a wavenumber spectrum and a frequency spectrum, which represent a composition and a structure of a sample during thermal analysis, and analysis of electromagnetic waves, which accompany a change in temperature, etc. are performed.

In order to solve the problems described above, the invention provides a thermal analysis equipment comprising in addition to a construction of a general thermal analysis equipment including a heating furnace that heats a sample, a temperature sensor that detects a temperature of the sample, a physical quantity sensors that detects a physical quantity of the sample varying as temperature changes, a temperature controller that controls a temperature of the heating furnace, and thermal analysis data preservation means that preserves, as data of thermal analysis, a set of signals from the temperature sensor and the physical quantity sensor, which is sampled at an appropriate time interval, electromagnetic-wave data acquisition means that acquires data of electromagnetic waves, which are obtained by detecting electromagnetic waves from the sample to digitize the same, electromagnetic-wave data acquisition trigger setting means that sets a trigger for acquisition of the data of electromagnetic waves, electromagnetic-wave data acquisition control means that controls acquisition of the data of electromagnetic waves according to a trigger set by the electromagnetic-wave data acquisition trigger setting means, and electromagnetic-wave data preservation means that preserves the acquired data of electromagnetic waves.

Wavelength object of those electromagnetic waves from a sample, which are acquired by the electromagnetic-wave data acquisition means, and data of electromagnetic waves comprise a sample picture, an object of which is a visible light, or a sample picture, an object of which is an infrared light or the like having a longer wavelength than that of a visible light, or a sample picture, an object of which is an ultraviolet light or the like having a shorter wavelength than that of a visible light.

Also, in some cases, data of electromagnetic waves acquired by the electromagnetic-wave data acquisition means comprise a so-called spectrum that outputs respective wavelength components or the strength of respective frequency components.

A trigger prescribes timing, in which data of electromagnetic waves are acquired, and sets timing, in which a change in data of electromagnetic waves is caught, or timing, in which data of electromagnetic waves are confirmed at a certain point on data of thermal analysis. Specifically, the following is set as a trigger.

(a) A specific time after the start of measurement, or at a time interval. In this case, a trigger such as "after 10 minutes after the start of measurement, after 12 minutes after the start of measurement, and at intervals of 5 minutes after the start of measurement", or the like is input in the electromagnetic-wave data acquisition trigger setting means, and a plurality of triggers can be set.

(b) The temperature sensor outputs a specific temperature or at a time interval. In this case, a trigger such as "100° C., 150° C., and 257° C., and intervals of 5° C. in the range of 100° C. to 250° C.", or the like is input in the electromagnetic-wave data acquisition trigger setting means, and a plurality of triggers can be set.

(c) The physical quantity sensor outputs a specific value or at a specific interval. In, for example, a thermomechanical analysis equipment, which is a kind of a thermal analysis equipment, a value caught by a physical value sensor is a sample length, or a rate of elongation-contraction, and a trigger is input as "500 µm, 750 µm, and an interval of 100 µm in the range of 800 µm to 1500 µm" or "90%, 100%, 130%, and an interval of 10% in the range of 150% to 200%", or the like in the electromagnetic-wave data acquisition trigger setting means. Also, in a differential scanning calorimeter, which is a further kind of a thermal analysis equipment, a value caught by a physical value sensor is a difference between a heating value, which goes in and out of a sample, and a heating value, which goes in and out of a reference substance, and a trigger is input as "100 µW, 150 µW, and an interval of 50 µW in the range of 300 µW to 800 µW", or the like in the electromagnetic-wave data acquisition trigger setting means, so that it is possible to set a plurality of triggers.

(d) The start or the termination of a region, in which a differential of an output of a physical value sensor is stable in a certain range for a predetermined period of time or longer. In, for example, a thermomechanical analysis equipment, the unit of a differential is µm/s and the range of a differential and a predetermined period of time are input as "1 minutes or longer within ±0.02 µm/s", or the like in the electromagnetic-wave data acquisition trigger setting means. In a differential scanning calorimeter, the unit of a differential is SW/s and the range of a differential is input as "1 minutes or longer within ±0.02 µW/s", or the like in the electromagnetic-wave data acquisition trigger setting means.

Further, in addition to the means described above, there can be also provided electromagnetic-wave data relating means that relates the data of electromagnetic waves, which are preserved when the trigger is generated, to a position on the data of thermal analysis, in which the trigger is generated, thermal analysis data display means that displays the data of thermal analysis, which are preserved in the thermal analysis data preservation means, in the form of a graph or the like on CRT, etc., thermal analysis data position indicating means that indicates an arbitrary point of a thermal analysis data graph displayed on the thermal analysis data display means, electromagnetic-wave data specifying means that according to relationship of a position indicated by the thermal analysis data position indicating means and the electromagnetic-wave data relating means, specifies the data of electromagnetic waves in the vicinity of an indicated position on the data graph of thermal analysis, out of the data of electromagnetic waves preserved in the electromagnetic-wave data preservation means, and electromagnetic-wave data composition output means that composes and outputs the specified data of electromagnetic waves as a sample picture, a frequency spectrum, etc. to the vicinity of a thermal analysis data graph, etc.

At this time, the electromagnetic-wave data relating means stores time when data of electromagnetic waves are preserved, a sample temperature, or the like as a key for relationship with data of thermal analysis, and stores a storage unit identifier in the electromagnetic-wave data preservation means, for example, a file name in case of a file system, and a main key of a record in case of database in order to specify data of electromagnetic waves corresponding to time or a sample temperature.

Also, at this time, the thermal analysis data position indication means includes a user interface, such as mouse, keyboard, etc., which indicates a position of data of thermal analysis displayed on CRT, or the like, and means that converts input from the user interface into a sample temperature on the data of thermal analysis and time.

BEST MODE FOR CARRYING OUT THE INVENTION

In a thermal analysis equipment constructed in the manner described above, a change in electromagnetic waves from a sample is found by setting a trigger, which is liable to generate a change in electromagnetic waves from a sample.

In the case where a change in electromagnetic waves from a sample is generated at a particular temperature, temperatures before and after such temperature are set as a trigger.

Also, in a thermomechanical analysis equipment, in the case where a change in electromagnetic waves from a sample is generated accompanying a change in a sample length, or the like, a plurality of triggers are set in a particular sample length, or at intervals of a sample length, or in a particular rate of elongation•contraction, or at intervals of a rate of elongation•contraction.

Also, in a thermomechanical analysis equipment, in the case where as a sample length expands at a constant speed, a change in electromagnetic waves from a sample is generated when a change in the speed of expansion is generated, or the like, the start or the termination of a region, in which a differential of a sample length is stable in a certain range for a predetermined period of time or longer, is set as a trigger. A value of a differential of a sample length is stable in a constant value where a sample length expands at a constant speed. A value of a differential is varied in a location, in which a change in the speed of expansion is generated, but the speed of expansion becomes stable and the differential becomes stable at a predetermined value. When the termination of a region, in which the differential becomes stable before the speed of expansion changes, and the start of a region, in which the differential becomes stable after the speed of expansion changes, are set as a trigger, it is possible to acquire data of electromagnetic waves before and after the speed of sample expansion changes. In a differential scanning calorimeter, in the case where a change in electromagnetic waves from a sample is generated as a sample melts, the start or the termination of a region, in which a differential of a caloric difference is stable in a certain range for a predetermined period of time or longer, is set as a trigger. Before melting of a sample begins, a caloric difference is maintained in equilibrium and a differential of the caloric difference is also stable in a certain range. When melting begins, a caloric difference changes in a direction, in which heat flows into a sample and the caloric difference increases, so that a differential of the caloric difference also varies. Along with the termination of melting the caloric difference returns to an equilibrium state and the differential of a caloric difference also becomes stable in a certain range. When the termination of a region, in which a differential is stable before melting, and the start of a region, in which the differential becomes stable after melting, are set as a trigger, it is possible to acquire data of electromagnetic waves before and after melting.

Also, in the case where a change in electromagnetic waves from a sample in no way leads to a change in sample temperature and physical value, or cannot be predicted, time of an appropriate interval is set as a trigger.

When a trigger corresponding to a change in data of electromagnetic waves from a sample is set in electromagnetic-wave data acquisition trigger setting means, a change in electromagnetic waves is found by using the electromagnetic-wave data acquisition control means to determine whether a condition of coincidence with a trigger is established during measurement, causing the electromagnetic-wave data acquisition control means to instruct electromagnetic-wave data acquisition means to acquire data of electromagnetic waves in case of coincidence with the set trigger, and feeding the acquired data of electromagnetic waves to electromagnetic-wave data preservation means to preserve the same therein.

Further, at the time of coincidence with a trigger set in the electromagnetic-wave data acquisition trigger setting means, electromagnetic-wave data acquisition control means instructs the electromagnetic-wave data acquisition means to acquire data of electromagnetic waves and transmits acquisition of data of electromagnetic waves to electromagnetic-wave data relating means. Receiving that, the electromagnetic-wave data relating means relates the present time or a sample temperature output from a temperature sensor to the name of a file for identification of data of electromagnetic waves on the electromagnetic-wave data preservation means to store the same. When data of thermal analysis are to be analyzed, data of thermal analysis preserved in the thermal analysis data preservation means are displayed on a CRT. In the case where it is desirable to confirm a singular point on data of thermal analysis, for example, data of electromagnetic waves nearly melting of a sample found by a differential scanning calorimeter, a user uses thermal analysis data position indicating means to indicate the singular point. The thermal analysis data position indicating means converts the singular point into a sample temperature and time to transmit the same to electromagnetic-wave data specifying means. The electromagnetic-wave data specifying means makes a comparison between the input sample temperature and time, and a sample temperature and time in the electromagnetic-wave data relating means to transmit that identifier of data of electromagnetic waves on the electromagnetic-wave data preservation means, which is caused to correspond to closest sample temperature and time, to electromagnetic-wave data composition output means. Receiving the identifier of data of electromagnetic waves, the electromagnetic-wave data composition output means displays those data of electromagnetic waves on the electromagnetic-wave data preservation means, which are identified by the identifier, that is, a sample picture, spectrum, etc. whereby data of electromagnetic waves corresponding to a singular point on data of thermal analysis.

Figure 1:
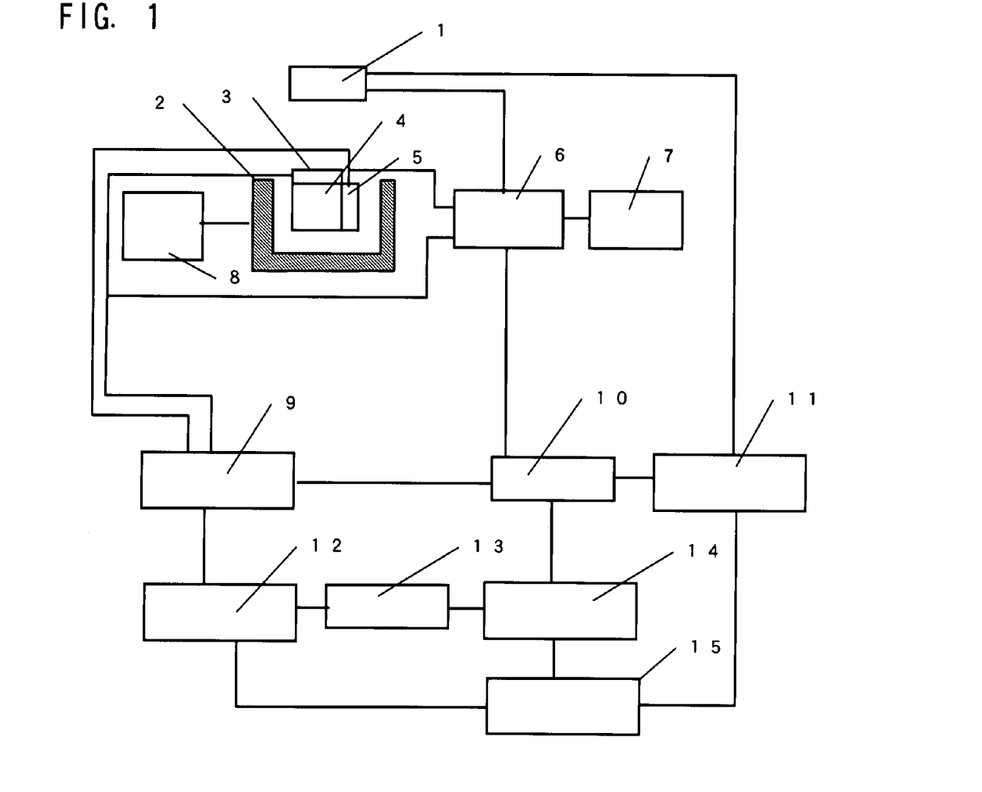
FIG. 1 is a view showing a construction of the invention.

An embodiment of the invention will be described with reference to the drawing 15. FIG. 1 is a view showing a construction of a thermal analysis equipment according to the invention. A user puts a sample 4 in a heating furnace 2 and the heating furnace 2 is controlled in temperature with a temperature controller 8 whereby the sample 4 is caused to undergo a desired temperature change. Temperature of the sample 4 is found by a temperature sensor 5 and the change in physical value, which accompanies a change in temperature, is found by a physical quantity sensor 3. A physical quantity as found differs every technique of thermal analysis such that a physical quantity found in thermomechanical analysis equipment is a sample length and a physical quantity found in differential scanning calorimetric analysis is a difference between a heating value, which goes in and out of a sample, and a heating value, which goes in and out of a reference substance. Also, in case of simultaneous measurement with a plurality of techniques of thermal analysis, plural physical quantity sensors 3 are provided to make simultaneous measurement of a plurality of physical values. Signals output from the temperature sensor 5 and the physical quantity sensors 3 are sampled at a time interval indicated by a user, or at an appropriate time interval judged by a system, or the like in thermal analysis data preservation means 9 to be preserved as data of thermal analysis, which are aligned as a set of sample temperature and physical quantity in a system or in a temperature system, in a file system or a data system.

Figure 2:
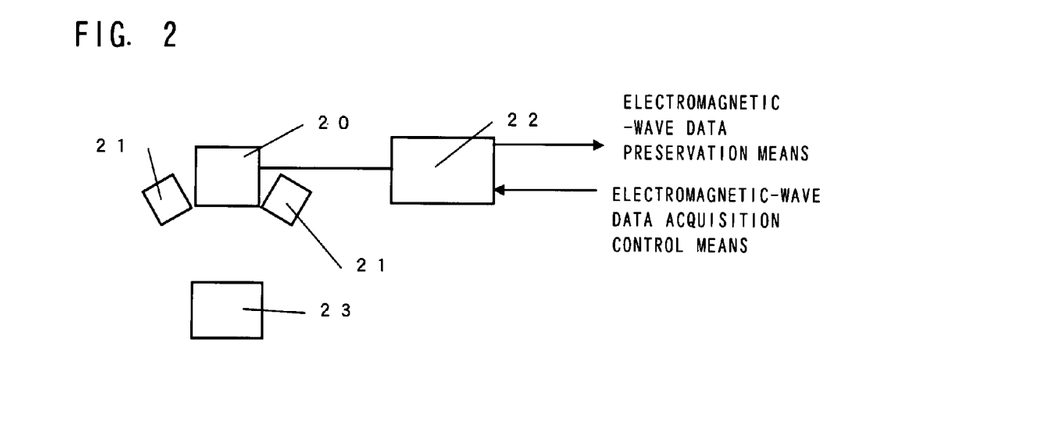
FIG. 2 is a view showing a construction of electromagnetic-wave data acquisition means, which acquires a sample picture.

Electromagnetic-wave data acquisition means 1 detects electromagnetic waves emitted by a sample upon a change in temperature and electromagnetic waves generated by irradiation of excited electromagnetic waves to acquire the electromagnetic waves as data of wavelength, intensity, etc. Electromagnetic waves as detected differ depending upon what change in a sample is found accompanying a change in temperature. In case of finding a change in outward appearance, a sample picture is acquired by irradiating a visible light on a sample and detecting a visible light reflected from the sample. Also, in case of finding a change in molecular structure and composition, an infrared light is irradiated on a sample and an infrared spectrum represented by wavelength and intensity of the reflected or transmitted infrared light is acquired. FIG. 2 shows an example of a construction of electromagnetic-wave data acquisition means in the case where a sample picture of a visible light is acquired as data of electromagnetic waves. An illumination 21 irradiates a visible light on a sample 23 and a camera 20 detects a visible light reflected from the sample 23 to transmit the same to a capture device 22. The capture device 22 converts an input from the camera 20 into digitized sample picture data in accordance with instructions from the electromagnetic-wave data acquisition control means to output the sample picture data to the electromagnetic-wave data preservation means.

Electromagnetic-wave data acquisition trigger setting means 7 causes a user to set timing, in which data of electromagnetic waves are caught, and timing, in which data of electromagnetic waves are confirmed at a certain point on data of thermal analysis. A trigger as input represents acquisition of data of electromagnetic waves when a value of data of thermal analysis meets a certain condition, and uses that condition for a change in data of thermal analysis, which predicts a change in data of electromagnetic waves.

In the case where the relationship between data of electromagnetic waves and a sample temperature is to be examined, or it is found that a change in data of electromagnetic waves will be generated at a particular temperature, a sample temperature is used as a trigger. In this case, indication is given by way of enumeration of particular temperatures such as "acquisition at 100° C., 150° C., and 257° C.", and intervals such as "acquisition at intervals of 5° C. in the range of 100° C. to 250° C." can be indicated.

In the case where the relationship between data of electromagnetic waves and physical quantities given by the physical quantity sensors 3 is to be examined, or it is found that a change in data of electromagnetic waves will be generated at a particular physical quantity, a physical quantity is used as a trigger. For example, in the case where an associated sample has a yield point at 150% of rate of elongation in thermomechanical analysis and a sample picture is acquired in order to confirm a sample shape roughly before the yield point and finely after the yield point, setting such as "acquisition at intervals of 25% below 140% or less and acquisition at intervals of 5% beyond 140%" is input.

Figure 3:
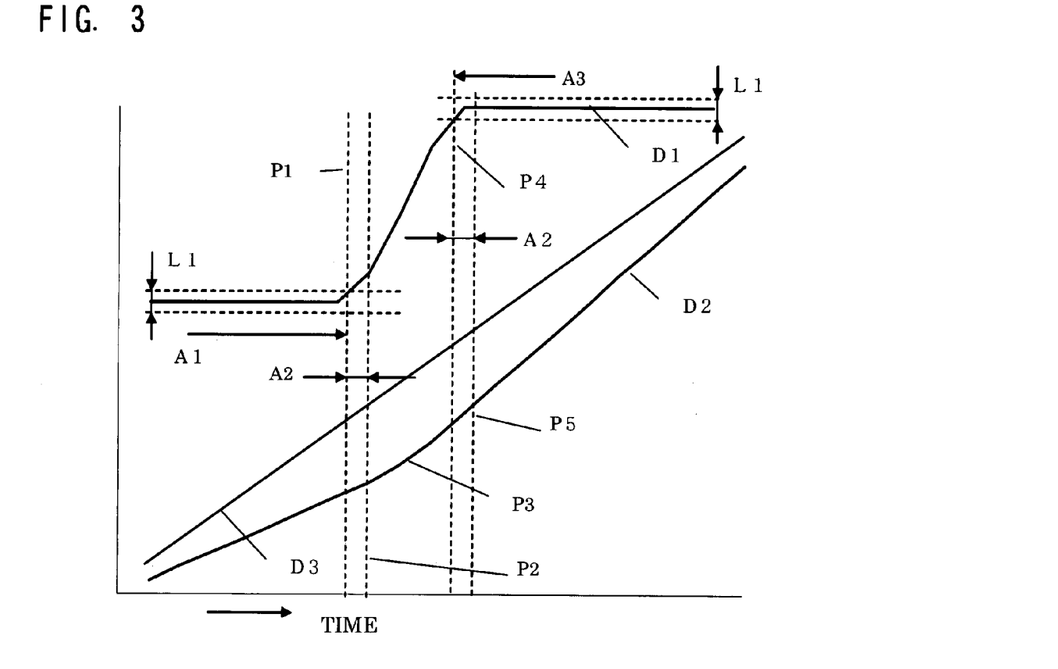
FIG. 3 is a view illustrating a differential trigger of a physical value in thermomechanical analysis.
Figure 4:
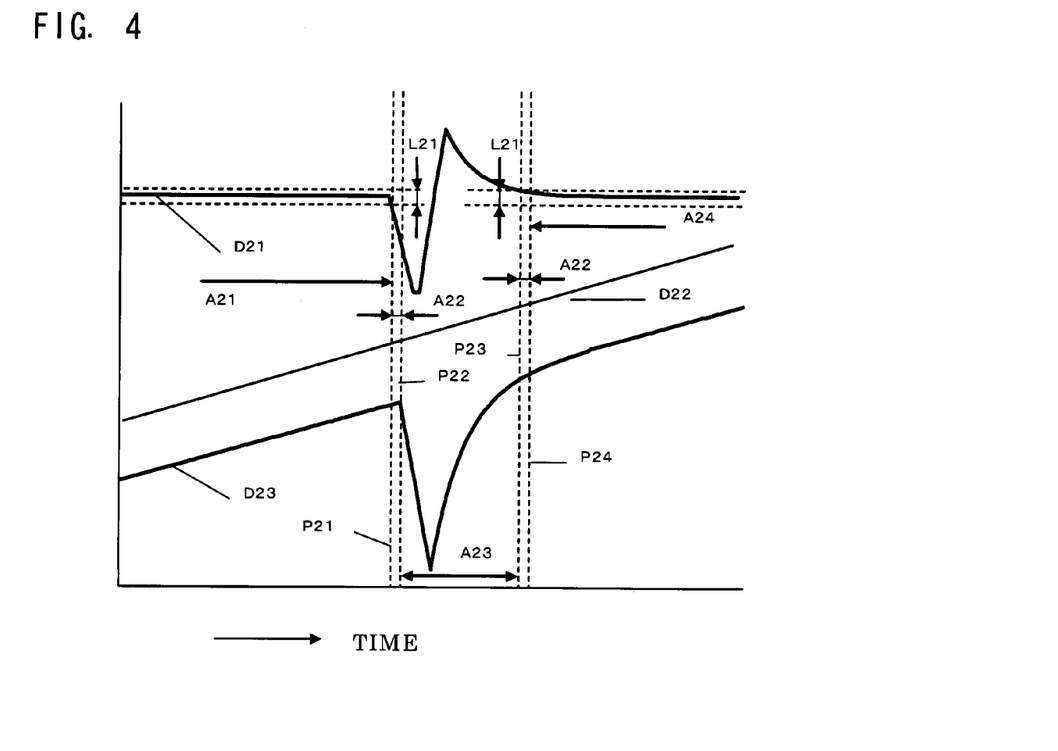
FIG. 4 is a view illustrating a differential trigger of a physical value in differential scanning calorimetric analysis.

In the case where the relationship between a change in data of electromagnetic waves and a change of a physical quantity per temperature or time is to be examined, or it is found that a change in data of electromagnetic waves is related to a change of a physical quantity per temperature or time, the start or the termination of a region, in which a differential of a physical quantity as a trigger is stable in a certain range for a predetermined period of time or longer, is used. For example, FIG. 3 shows data of thermal analysis before and after a glass transition point, at which a high polymer changes to a rubber state from a glass state in the course of temperature rise, in thermomechanical analysis, and it is thought that some change in data of electromagnetic waves appears before and after the glass transition point. In FIG. 3, at the time of temperature rise like a sample temperature D3, variation of a sample length D2 output from the physical quantity sensors in thermomechanical analysis changes before and after a glass transition point P3. At this time, a differential D1 of a sample length D2 changes stepwise. In the case where the differential D1 is in a differential range L1 centering on an average in a certain zone of the differential D1 for a predetermined period of time A2 or longer, a region is determined, in which a differential is stable as in a pre-glass transition differential stable region A1 and a post-glass transition differential stable region A2. In the case where the start or the termination of a region, in which a differential becomes stable, is indicated as a trigger, data of electromagnetic waves are acquired at P2 and P5, which are a predetermined period of time A2 later behind a point P1 of termination of the pre-glass transition differential stable region and a point P4 of start of the post-glass transition differential stable region. Shifts between P1 and P2 and between P4 and P5 are generated since the predetermined period of time A2 is needed for determination of whether a differential is stable or not. In thermomechanical analysis, in the case where the start or the termination of a region, in which a differential of a sample length is stable in a certain range for a predetermined period of time or longer, is used as a trigger, the electromagnetic-wave data acquisition trigger setting means 7 makes setting such as "a starting point and a terminating point oft minor longer within ±0.02 µm/s". FIG. 4 shows data of thermal analysis before and after melting, in which a high polymer changes to a liquid phase from a solid phase in the course of temperature rise, in differential scanning calorimetric analysis, and it is thought that some change in data of electromagnetic waves appears before and after melting. In particular, a change in a sample picture, such as a change, in which a granular solid becomes liquid, is found. In FIG. 4, at the time of temperature rise like a sample temperature D22, an endothermic peak, in which heat flows into a sample, appears in a calorimetric difference D23, which is output from the physical quantity sensors in differential scanning calorimetric analysis, in a melting region A23. At this time, a differential D21 of the calorimetric difference D23 decreases from a stable region and then increases to get again in a stable region. In the case where the differential D21 is in a differential range D21 centering on an average in a certain zone of the differential D21 for a predetermined period of time A22 or longer, a region is determined, in which a differential is stable as in a pre-glass melting differential stable region A21 and a post-melting differential stable region A24. In the case where the start or the termination of a region, in which a differential becomes stable, is indicated as a trigger, data of electromagnetic waves are acquired at P22 and P24, which are a predetermined period of time A22 later behind a point P21 of termination of the pre-melting differential stable region and a point P23 of start of the post-melting differential stable region. In differential scanning calorimetric analysis, in the case where the start or the termination of a region, in which a differential of a calorimetric difference is stable in a certain range for a predetermined period of time or longer, is used as a trigger, the electromagnetic-wave data acquisition trigger setting means 7 makes setting such as "a starting point and a terminating point of 1 min or longer within ±0.02 µW/s".

In the case where the relationship between data of electromagnetic waves and a sample temperature and a physical quantity or a differential of a physical quantity is in no way known, time is used as a trigger. In this case, indication is given by way of enumeration of a particular time such as "acquisition after 10 minutes after the start of measurement, and acquisition after 12 minutes after the start of measurement" and intervals such as "acquisition at intervals of 5 minutes since the start of measurement" can be indicated.

The electromagnetic-wave data acquisition control means 6 makes a comparison between outputs of the temperature sensor 5 and the physical quantity sensor 3 and a trigger set by the electromagnetic-wave data acquisition trigger setting means 7 during measurement to determine whether a condition set by the present trigger is met. In case of coincidence, the electromagnetic-wave data acquisition control means 6 instructs the electromagnetic-wave data acquisition means 1 to acquire data of electromagnetic waves and feeds acquisition of data of electromagnetic waves, a sample temperature at that time, and time elapsed after the start of measurement to the electromagnetic-wave data relating (correlation) means 10.

The electromagnetic-wave data preservation means 11 preserves data of electromagnetic waves transmitted from the electromagnetic-wave data acquisition means 1 whenever acquired. In the case where a destination of preservation is a file system, data of electromagnetic waves are preserved in one file whenever acquired, and in the case where a destination of preservation is a database system, data of electromagnetic waves are preserved in one record whenever acquired. Normally, since a plurality of and further several tens of data of electromagnetic waves are preserved in one thermal analysis measurement, it is possible to provide a commitment indicative of data of electromagnetic waves in the same thermal analysis measurement. For example, in the case where a destination of preservation is a file system, it is possible to provide the following commitment.

(a) Used as a file name of data of electromagnetic waves is an addition of the number of times of acquisition of data of electromagnetic waves in thermal analysis measurement, to a file of data of thermal analysis being preserved in the thermal analysis data preservation means 9.

(b) Used as a directory name of a destination of preservation of data of electromagnetic waves is a file name of data of thermal analysis being preserved in the thermal analysis data preservation means 9.

The electromagnetic-wave data relating means 10 creates and stores related data so that a sample temperature at the time of acquisition of data of electromagnetic waves transmitted from the electromagnetic-wave data acquisition control means 6, time elapsed after the start of measurement, and a storage unit identifier in the electromagnetic-wave data preservation means 11 are made a set and data of electromagnetic waves can be thereafter related from a sample temperature on data of thermal analysis or time. The storage unit identifier is a file name when a destination of preservation of data of electromagnetic waves is a file name, and a main key of a record when the destination is a database. For example, with a file system, related data in the electromagnetic-wave data relating means 10 are created in the form of "100° C. 10 min file name of data of electromagnetic waves", or the like. Further, such related data are stored in the following site so that it can be followed from data of thermal analysis.

(a) Related data are transmitted to the thermal analysis data preservation means 9 to be stored as a part of data of thermal analysis.

(b) A commitment affording to follow preservation of related data from data of thermal analysis is made and stored. For example, a directory having a name of a file of data of thermal analysis is created in a predetermined directory as a destination of preservation of related data and related data is preserved therein.

Thermal analysis data display means 12 displays, on a display device such as CRT, etc., data of thermal analysis preserved in the thermal analysis data preservation means 9 in the form of a two-dimensional graph with a sample temperature or time on an axis of abscissas and a physical quantity on an axis of ordinates.

Thermal analysis data position indication means 13 includes a user interface, such as mouse, keyboard, etc., which indicates data of thermal analysis displayed on the thermal analysis data display means 12, and converts positional information input from the user interface into a sample temperature and time on data of thermal analysis to transmit a sample temperature and time to electromagnetic-wave data specifying means 14. A position being indicated can include a plurality of locations.

Figure 5:
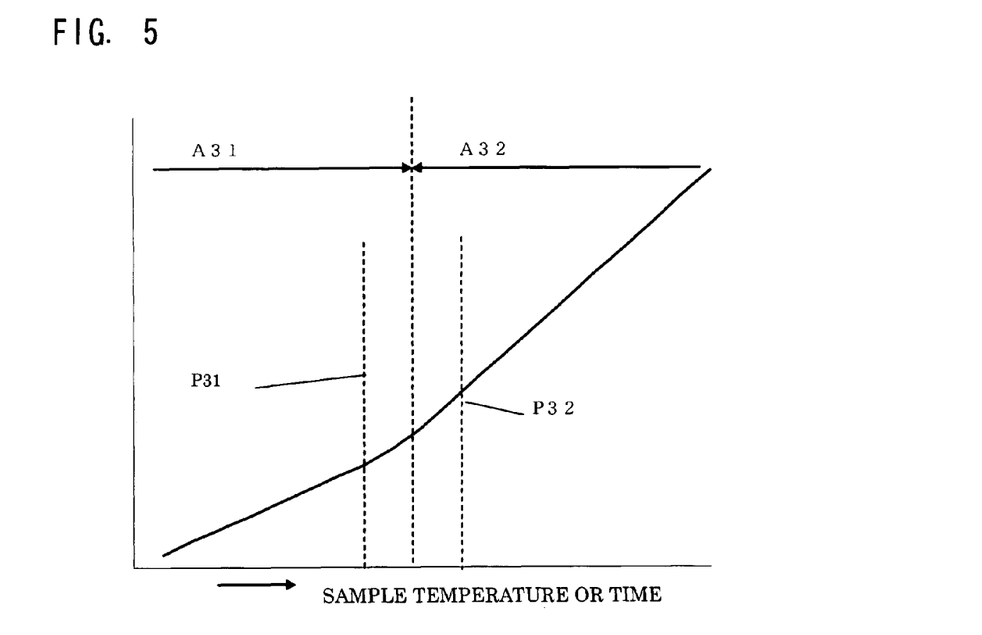
FIG. 5 is a view illustrating indication of positions of data of thermal analysis and specified data of electromagnetic waves.

The electromagnetic-wave data specifying means 14 makes a comparison between a plurality of sample temperatures and time indicated by the thermal analysis data position indication means 13 and a sample temperature and time on related data stored in a plurality of electromagnetic-wave data relating means 10 specified from data of thermal analysis as displayed, and specifies an identifier of data of electromagnetic waves in the electromagnetic-wave data preservation means 11 indicated by related data, which are close to the indicated sample temperature and time. For example, in the case where data of electromagnetic waves are acquired at two points P31 and P32 in data of thermal analysis in FIG. 5, data of electromagnetic waves acquired at P31 are specified when a range A31 is indicated by the thermal analysis data position indication means 13, and data of electromagnetic waves acquired at P32 are specified when a range A32 is indicated by the thermal analysis data position indication means 13.

Electromagnetic-wave data composition output means 15 composes a plurality of data of electromagnetic waves specified by the electromagnetic-wave data specifying means 14 and data of thermal analysis to display the same on a display device such as CRT, printer, etc. and an output device, and outputs in the following form.

Figure 6:
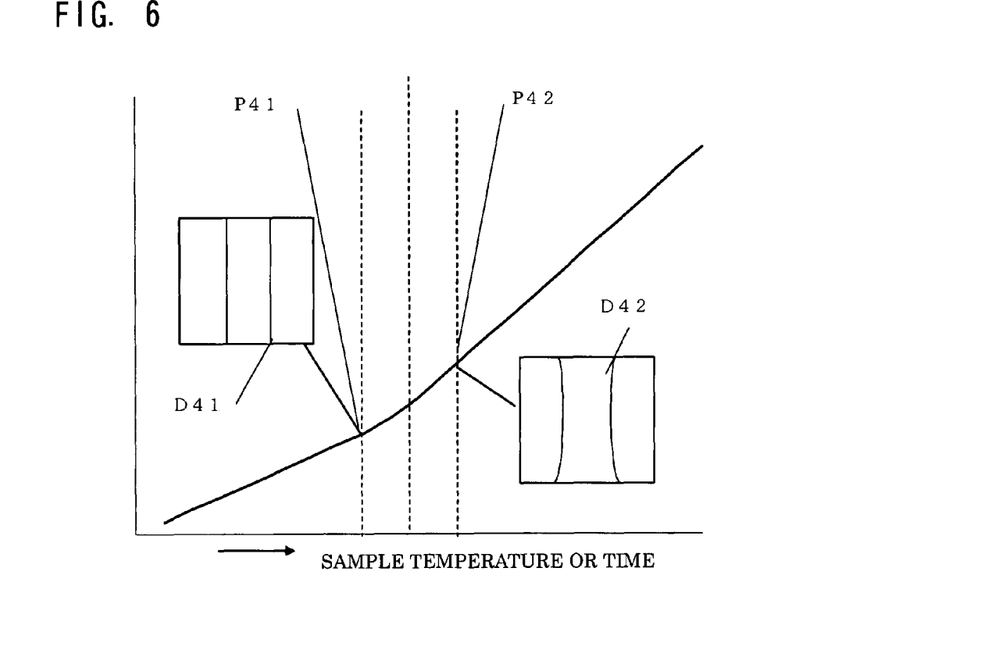
FIG. 6 is a view illustrating a first example, in which data of electromagnetic waves are composed and output.

(a) Exemplarily shown in FIG. 6, data of electromagnetic waves (D41 and D42) are composed and output into data of thermal analysis in the vicinity of those positions (P41 and P42) of data of thermal analysis, in which data of electromagnetic waves are acquired.

Figure 7:
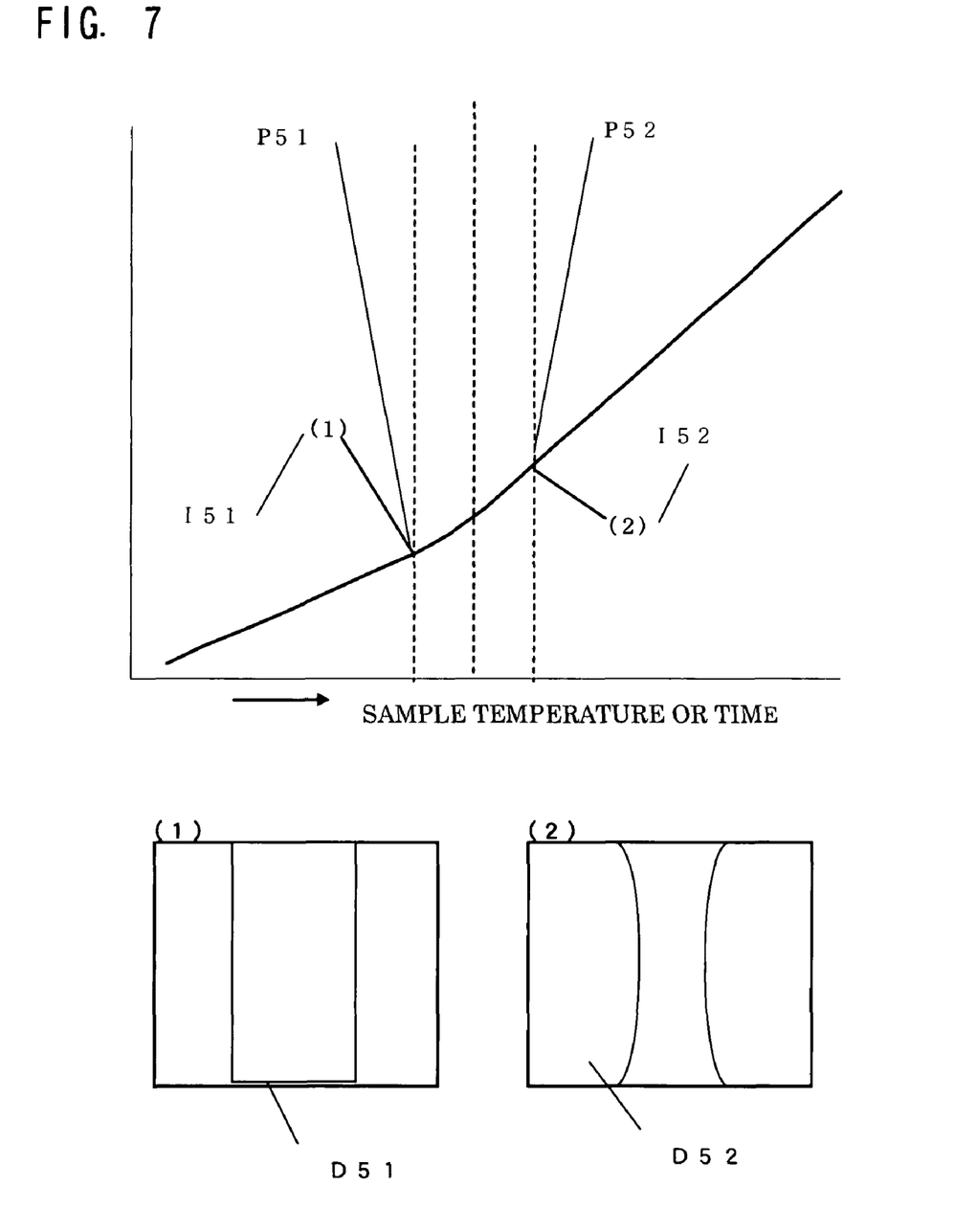
FIG. 7 is a view illustrating a second example, in which data of electromagnetic waves are composed and output.

(b) Exemplarily shown in FIG. 7, blowouts (I51 and I52) indicative of the relationship with data of electromagnetic waves are composed and output outside data of thermal analysis in the vicinity of those positions (P51 and P52) of data of thermal analysis, in which data of electromagnetic waves are acquired.

Subsequently, an explanation will be given to a contrivance for an improvement on shift between a point of termination of a region, in which an actual differential is stable, and a point, at which data of electromagnetic waves are acquired, so that shifts between P1 and P2 and between P4 and P5 in FIG. 3 are generated when the start or the termination of a region, in which a differential of a physical quantity is stable in a certain range for a predetermined period of time or longer, is used as a trigger.

As countermeasures for such shift, data of electromagnetic waves are first acquired at a predetermined cycle and the acquired data of electromagnetic waves are successively preserved in a temporary buffer. Since the start and the termination of a region, in which a differential is stable, are found after a predetermined period of time, data of electromagnetic waves beyond the period of time are immediately preserved in the buffer, the necessary data of electromagnetic waves are taken out from the buffer after the start and the termination are found, and data of electromagnetic waves not taken out are erased after the lapse of a predetermined period of time.

An explanation will be given to the case where, for example, such buffer is provided in the electromagnetic-wave data preservation means 11.

Figure 8:
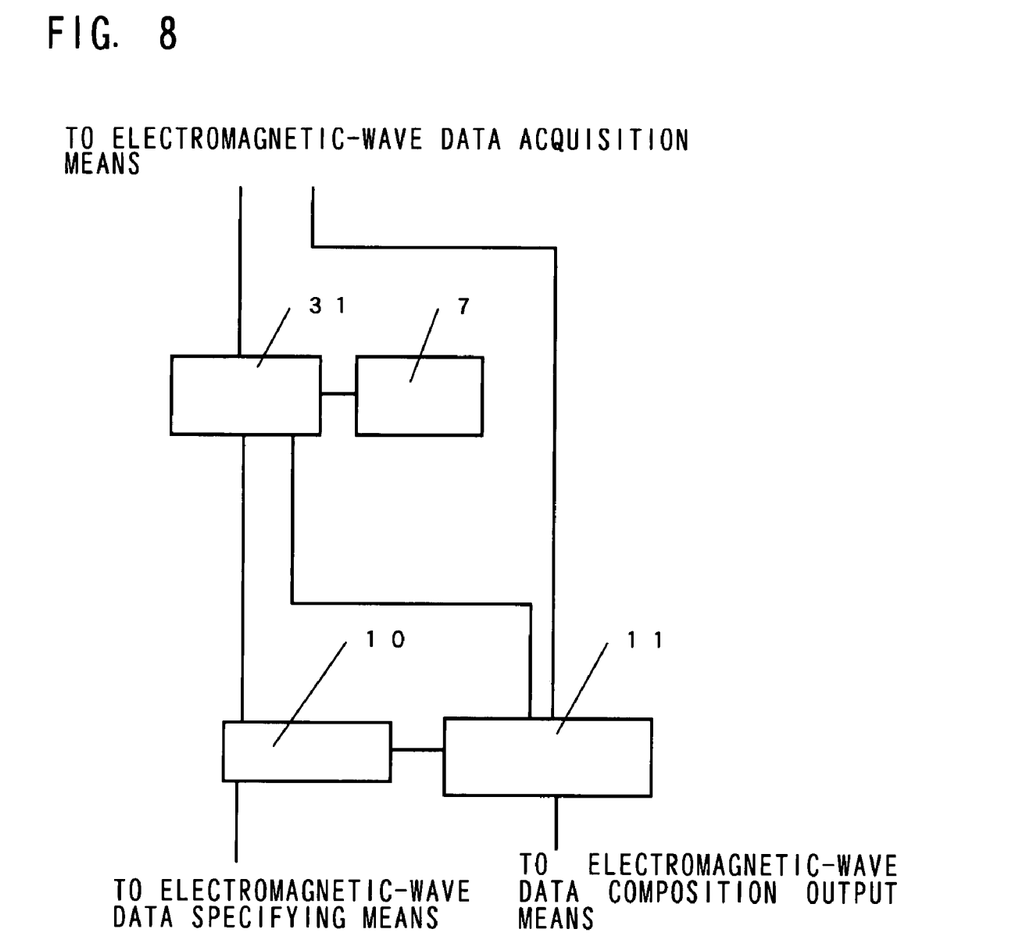
FIG. 8 is a view showing a part of a construction, in which further electromagnetic-wave data acquisition control means according to the invention is used.

In order to provide a buffer in the electromagnetic-wave data preservation means 11, the electromagnetic-wave data acquisition control means 6 is contrived to be changed into electromagnetic-wave data acquisition control means 31. FIG. 8 shows such construction. Except that the electromagnetic-wave data acquisition control means 31 is connected to the electromagnetic-wave data preservation means 11, functions of the electromagnetic-wave data acquisition trigger setting means 7, the electromagnetic-wave data relating means 10, and the electromagnetic-wave data preservation means 11, other functions, and the relationship of connection remain unchanged.

The electromagnetic-wave data acquisition control means 31 always instructs the electromagnetic-wave data acquisition means 1 in a predetermined cycle to acquire data of electromagnetic waves. Accordingly, data of electromagnetic waves are successively preserved in the electromagnetic-wave data preservation means 11. Therefore, after the lapse of a predetermined period of time after data of electromagnetic waves are preserved, the electromagnetic-wave data acquisition control means 31 erases those data of electromagnetic waves, which do not correspond to a trigger set by the electromagnetic-wave data acquisition trigger setting means 7. Also, when the start or the termination of a region, in which a differential of a physical quantity is stable in a certain range for a predetermined period of time or longer, is used as a trigger, a starting point and a terminating point of a region, in which a differential is stable, are retroacted in time to make a location, in which stability begins to terminate, or stability begins to start, a point, which corresponds to a trigger.

Figure 9:
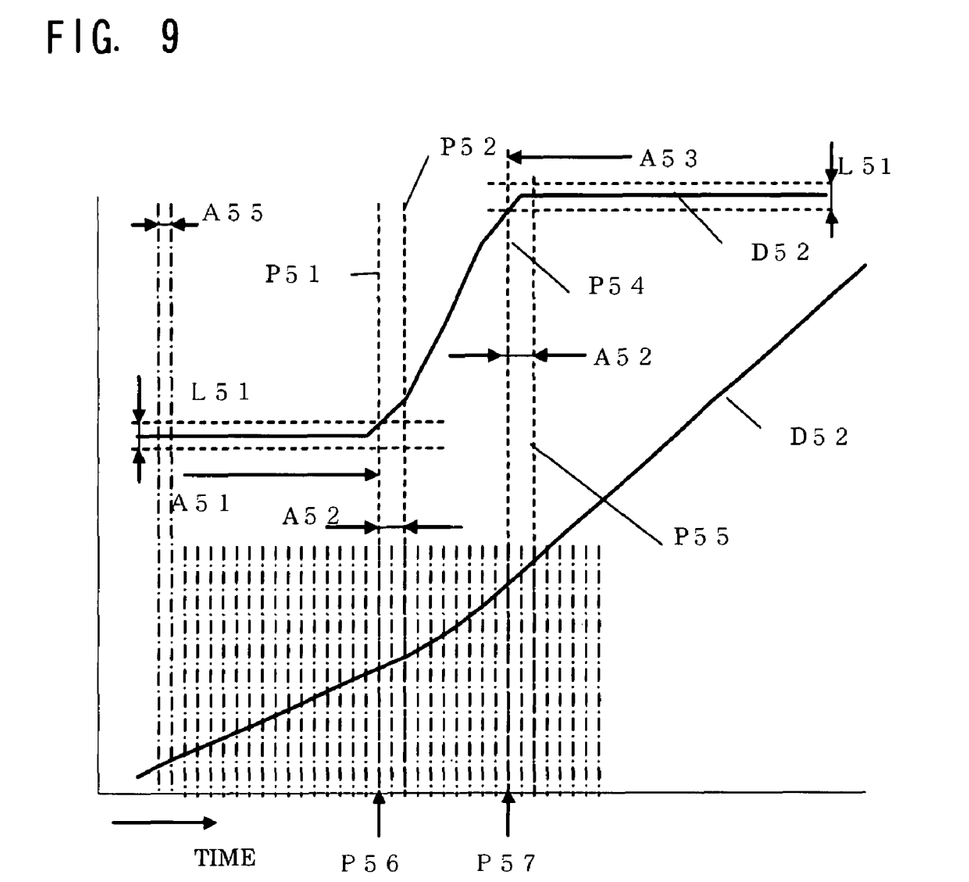
FIG. 9 is a view illustrating a differential trigger of a physical value in thermomechanical analysis in the construction shown in FIG. 8.

An action of the electromagnetic-wave data acquisition control means 31 before and after a glass transition point in thermomechanical analysis will be described with reference to FIG. 9. The electromagnetic-wave data acquisition control means 31 always instructs the electromagnetic-wave data acquisition means 1 as in a predetermined cycle A55 to acquire data of electromagnetic waves in FIG. 3. When the electromagnetic-wave data acquisition control means 31 detects a point P52, at which a differential D52 gets out of a differential range L51 for a predetermined period A52 of time or longer, a point P51, at which getting-out from the differential range L51 begins, is retroacted and made a pre-glass transition differential stable region terminating point P56. Also, when the electromagnetic-wave data acquisition control means 31 detects a point P55, at which a differential D52 is present outside the differential range L51 for a predetermined period A52 of time or longer, a point P54, at which presence in the differential range L51 begins, is retroacted and made a post-glass transition differential stable region terminating point P57. After the predetermined period A52 of time or longer has lapsed since the present time, data of electromagnetic waves acquired in a predetermined cycle A55, which is not recognized by a trigger, are erased. Necessary information is fed to the electromagnetic-wave data relating means 10 at a point of time when a point, such as the pre-glass transition differential stable region terminating point P56 and the post-glass transition differential stable region terminating point P57, which corresponds to a trigger, is detected.

By doing this, data of electromagnetic waves are acquired at the pre-glass transition differential stable region terminating point P56 and the post-glass transition differential stable region terminating point P57, so that shifts between P1 and P2 and between P4 and P5 in FIG. 3 disappear.

INDUSTRIAL APPLICABILITY

The invention produces the following effects.

A thermal analysis equipment, which acquires data of electromagnetic waves from a sample, comprises electromagnetic-wave data acquisition trigger setting means and electromagnetic-wave data acquisition control means whereby a change in data of electromagnetic waves, to which it is desirable to pay attention, can be caught without preserving data of electromagnetic waves over whole limits of measuring time in thermal analysis.

Also, when data of electromagnetic waves comprise a sample picture of visible light or a sample picture of light, such infrared light, etc., except a visible light, a change in a sample picture, to which it is desirable to pay attention, can be caught without preserving sample pictures over whole limits of measuring time in thermal analysis.

Also, when data of electromagnetic waves comprise a spectrum, a change in a sample spectrum, to which it is desirable to pay attention, can be caught without preserving spectra over whole limits of measuring time in thermal analysis.

Further, in the case where a trigger set in electromagnetic-wave data acquisition trigger setting means comprises a plurality of periods of time since the start of analysis, or time intervals, a change in data of electromagnetic waves can be caught, without preserving data of electromagnetic waves over whole limits of measuring time in thermal analysis, for a sample, in which a change in data of electromagnetic waves does not lead to a change in sample temperature and physical quantity, and for a sample, in which a change in data of electromagnetic waves from the sample and a change in sample temperature and physical quantity are not confirmed.

Also, when a trigger set in electromagnetic-wave data acquisition trigger setting means comprises a specified sample temperature or a temperature interval, a change in data of electromagnetic waves, to which it is desirable to pay attention, can be caught, without preserving data of electromagnetic waves over whole limits of measuring time in thermal analysis, for a sample, in which a change in data of electromagnetic waves is generated at a specified temperature.

Also, when a trigger set in electromagnetic-wave data acquisition trigger setting means comprises a specified value of a signal of a physical value sensor or an interval, a change in data of electromagnetic waves, to which it is desirable to pay attention, can be caught, without preserving data of electromagnetic waves over whole limits of measuring time in thermal analysis, for a sample, in which a change in data of electromagnetic waves is generated at a specified physical value of a sample.

Also, when a trigger set in electromagnetic-wave data acquisition trigger setting means comprises the start or the termination of a region, in which a differential of a signal of a physical value sensor is stable in a certain range for a predetermined period of time or longer, a change in data of electromagnetic waves, to which it is desirable to pay attention, can be caught, without preserving data of electromagnetic waves over whole limits of measuring time in thermal analysis, for a sample, in which a change in data of electromagnetic waves is generated upon a change in physical value of a sample. In this case, since data of electromagnetic waves are acquired without deciding a specified physical value, one trigger makes it possible to acquire data of electromagnetic waves even in the case where a plurality of changes in data of electromagnetic waves are generated upon a change in physical value of a sample, or an unknown location or locations of change are present.

Further, the electromagnetic-wave data relating means, the thermal analysis data display means, the thermal analysis data position indicating means, the electromagnetic-wave data specifying means, and the electromagnetic-wave data composition output means are provided whereby a sample picture related to that point on data of thermal analysis, to which attention is paid, is quickly extracted from many sample pictures to enable readily realizing a report even in the case where sample pictures and data of thermal analysis are combined together after measurement to make a report or the like.

The invention claimed is:

1. A thermal analysis equipment for performing thermal analysis, the thermal analysis equipment comprising:
   a heating furnace that heats a sample;
   a temperature controller that controls a temperature of the heating furnace;
   a temperature sensor that detects a temperature of the sample;
   a physical quantity sensor that detects a change in physical quantity of the sample;
   thermal analysis data preservation means for preserving, as thermal analysis data, signals from the temperature sensor and the physical quantity sensor;
   electromagnetic-wave data acquisition means for acquiring electromagnetic wave data obtained by detecting electromagnetic waves from the sample;

electromagnetic-wave data acquisition trigger setting means for setting a trigger to acquire the electromagnetic wave data;

electromagnetic-wave data acquisition control means for controlling acquisition of the electromagnetic wave data in accordance with setting of the trigger by the electromagnetic-wave data acquisition trigger setting means;

electromagnetic-wave data preservation means for preserving the electromagnetic wave data; and electromagnetic-wave data correlation means for correlating the preserved electromagnetic wave data to a position on the thermal analysis data obtained by a thermal analysis data position indicating means obtained by a thermal analysis data position indicating means when the trigger is set by the electromagnetic-wave data acquisition trigger setting means.

2. A thermal analysis equipment according to claim 1; wherein the electromagnetic wave data acquired by the electromagnetic-wave data acquisition means comprises a sample picture of visible light or a sample picture of light except for visible light.

3. A thermal analysis equipment according to claim 1; wherein the electromagnetic wave data acquired by the electromagnetic-wave data acquisition means comprises a spectrum of respective wavelength components or of a strength of respective wavelength components of the electromagnetic-wave data.

4. A thermal analysis equipment according to claim 1; wherein the electromagnetic-wave data acquisition trigger setting means sets the trigger for a plurality of times after the start of a thermal analysis or sets the trigger at specific time intervals after the start of the thermal analysis.

5. A thermal analysis equipment according to claim 1; wherein the electromagnetic-wave data acquisition trigger setting means sets the trigger for a plurality of specified temperatures or temperature intervals corresponding to sample temperatures detected by the temperature sensor.

6. A thermal analysis equipment according to claim 1; wherein the electromagnetic-wave data acquisition trigger setting means sets the trigger for a plurality of specified values or signal intervals corresponding to the change in physical value of the sample detected by the physical quantity sensor.

7. A thermal analysis equipment according to claim 1; wherein the electromagnetic-wave data acquisition trigger setting means sets the trigger to the start or the termination of a region in which a differential of a signal from the physical quantity sensor stable in a certain range for at least a predetermined period of time.

8. A thermal analysis equipment according to claim 1; further comprising:

thermal analysis data display means for displaying the thermal analysis data preserved by the thermal analysis data presentation means;

thermal analysis data position indicating means for indicating on the thermal analysis data displayed by the thermal analysis data display means an arbitrary position corresponding to the position on the thermal analysis data to which the electromagnetic wave data is correlated by the electromagnetic-wave data correlation means;

electromagnetic-wave data specifying means for specifying electromagnetic wave data, which is presented by the electromagnetic-wave data preservation means, in the vicinity of the arbitrary position indicated by the thermal analysis data position indicating means; and electromagnetic-wave data output means for outputting the specified electromagnetic wave data into the thermal analysis data display means.

9. A thermal analysis equipment according to claim 2; wherein the electromagnetic-wave data acquisition trigger setting means sets the trigger for a plurality of times after the start of a thermal analysis or sets the trigger at specific time intervals after the start of the thermal analysis.

10. A thermal analysis equipment according to claim 2; wherein the electromagnetic-wave data acquisition trigger setting means sets the trigger for a plurality of specified temperatures or temperature intervals corresponding to sample temperatures detected by the temperature sensor.

11. A thermal analysis equipment according to claim 2; wherein the electromagnetic-wave data acquisition trigger setting means sets the trigger for a plurality of specified values or signal intervals corresponding to the change in physical value of the sample detected by the physical quantity sensor.

12. A thermal analysis equipment according to claim 2; wherein the electromagnetic-wave data acquisition trigger setting means sets the trigger to the start or the termination of a region in which a differential of a signal from the physical quantity sensor is stable in a certain range for at least a predetermined period of time.

13. A thermal analysis equipment according to claim 2; further comprising:

thermal analysis data display means for displaying the thermal analysis data preserved by the thermal analysis data preservation means;

thermal analysis data position indicating means for indicating on the thermal analysis data displayed by the thermal analysis data display means an arbitrary position corresponding to the position on the thermal analysis data to which the electromagnetic wave data is correlated by the electromagnetic-wave data correlation means;

electromagnetic-wave data specifying means for specifying electromagnetic wave data, which is preserved by the electromagnetic-wave data preservation means, in the vicinity of the arbitrary position indicated by the thermal analysis data position indicating means; and electromagnetic-wave data output means for outputting the specified electromagnetic wave data into the thermal analysis data display means.

14. A thermal analysis equipment according to claim 2; wherein the electromagnetic wave data comprises a sample picture of infrared light.

15. A thermal analysis equipment according to claim 3; wherein the electromagnetic-wave data acquisition trigger setting means sets the trigger for a plurality of times after the start of a thermal analysis or sets the trigger at specific time intervals after the start of the thermal analysis.

16. A thermal analysis equipment according to claim 3; wherein the electromagnetic-wave data acquisition trigger setting means sets the trigger for a plurality of specified temperatures or temperature intervals corresponding to sample temperatures detected by the temperature sensor.

17. A thermal analysis equipment according to claim 3; wherein the electromagnetic-wave data acquisition trigger setting means sets the trigger for a plurality of specified values or signal intervals corresponding to the change in physical value of the sample detected by the physical quantity sensor.

18. A thermal analysis equipment according to claim 3; wherein the electromagnetic-wave data acquisition trigger setting means sets the trigger to the start or the termination of a region in which a differential of a signal from the physical quantity sensor is stable in a certain range for at least a predetermined period of time.

19. A thermal analysis equipment according to claim 3; further comprising:

thermal analysis data display means for displaying the thermal analysis data preserved by the thermal analysis data preservation means;

thermal analysis data position indicating means for indicating on the thermal analysis data displayed by the thermal analysis data display means an arbitrary position corresponding to the position on the thermal analysis data to which the electromagnetic wave data is correlated by the electromagnetic-wave data correlation means;

electromagnetic-wave data specifying means for specifying electromagnetic wave data, which is preserved by the electromagnetic-wave data preservation means, in the vicinity of the arbitrary position indicated by the thermal analysis data position indicating means; and electromagnetic-wave data output means for outputting the specified electromagnetic wave data into the thermal analysis data display means.

\* \* \* \* \*